(12) United States Patent
Mjalli et al.

(10) Patent No.: US 8,350,039 B2
(45) Date of Patent: Jan. 8, 2013

(54) SUBSTITUTED ISOQUINOLINE DERIVATIVES, PHARMACEUTICAL COMPOSITIONS, AND METHODS OF USE AS BETA-SECRETASE INHIBITORS

(75) Inventors: Adnan M. M. Mjalli, Oak Ridge, NC (US); Bapu Gaddam, High Point, NC (US); Devi Reddy Gohimukkula, Jamestown, NC (US); Dharma Rao Polisetti, High Point, NC (US); Hassan El Abdellaoui, Jamestown, NC (US); Mohan Rao, Greensboro, NC (US); Pingzhen Wang, Kernersville, NC (US); Robert Carl Andrews, Jamestown, NC (US); Rongyuan Xie, Greensboro, NC (US); Tan Ren, Colfax, NC (US)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 13/214,434

(22) Filed: Aug. 22, 2011

(65) Prior Publication Data

US 2012/0101125 A1      Apr. 26, 2012

Related U.S. Application Data

(63) Continuation of application No. PCT/US2010/031743, filed on Apr. 20, 2010.

(60) Provisional application No. 61/173,176, filed on Apr. 27, 2009.

(51) Int. Cl.
 C07D 217/26 (2006.01)
 A61K 31/472 (2006.01)
 A61K 31/4725 (2006.01)
 A61P 25/28 (2006.01)

(52) U.S. Cl. ........................................ 546/146; 514/307

(58) Field of Classification Search .......................... None
 See application file for complete search history.

(56) References Cited

U.S. PATENT DOCUMENTS

| | | |
|---|---|---|
| 6,696,437 B1 | 2/2004 | Lubisch et al. |
| 7,338,956 B2 | 3/2008 | Strobel et al. |
| 7,893,267 B2 | 2/2011 | Mjalli et al. |
| 2002/0123484 A1 | 9/2002 | Das et al. |
| 2003/0134854 A1 | 7/2003 | Flohr et al. |
| 2003/0236267 A1 | 12/2003 | Kobayashi et al. |
| 2006/0223849 A1 | 10/2006 | Mjalli et al. |
| 2011/0065713 A1 | 3/2011 | Mjalli et al. |
| 2012/0101093 A1 | 4/2012 | Mjalli et al. |
| 2012/0101125 A1 | 4/2012 | Mjalli et al. |

FOREIGN PATENT DOCUMENTS

| | | |
|---|---|---|
| WO | WO 01/00611 | 1/2001 |
| WO | WO 01/21615 | 3/2001 |
| WO | WO 02/069965 | 9/2002 |
| WO | WO 03/032984 | 4/2003 |
| WO | WO 03/041708 | 5/2003 |
| WO | WO 03/053939 | 7/2003 |
| WO | WO 03/075921 | 9/2003 |
| WO | WO 2004/014369 | 2/2004 |
| WO | WO 2006/099379 | 9/2006 |

OTHER PUBLICATIONS

Richard B. Silverman, The Organic Chemistry of Drug Design and Drug Action, Chapter 2: Drug Discovery, Design, and Development, Academic Press, p. 5-51 (1992).*
International Preliminary Report on Patentability and Written Opinion for Application No. PCT/US2010/031743, mailed Nov. 10, 2011.
PCT International Search Report and Written Opinion for Application No. PCT/US2010/031743, mailed Jun. 17, 2010.
Cheng et al., "Synthesis and Antiviral Activity Against Coxsackie Virus B3 of some Novel Benzimidazole Derivatives" Bioorganic & Medicinal Chemistry Letters, 15(2):267-269 (2005).
Denny, et al., "Potential Antitumor Agents" Journal of Medicinal Chemistry, 33(2):814-819 (1990).
Ghosh et al., "Potent Memapsin 2 (beta-Secretase) Inhibitors: Design, Synthesis, Protein-Ligand X-ray Structure and in Vivo Evaluation" Bioorganic & Medicinal Chemistry Letters, 18(3):1031-1036 (2008).
Silverman, The Organic Chemistry of Drug Action, 2nd Ed., Elsevier Academic Press, Burlington, MA, pp. 29-34 (2004).
Silvestri, "Boom in the Development of Non-Peptidic Beta-Secretase (BACE1) Inhibitors for the Treatment of Alzheimer's Disease" Medicinal Research Reviews, 29(2):295-338 (2009).
Wermuth, The Practice of Medicinal Chemistry, Chapter 13: Molecular Variations Based on Isosteric Replacements, 2nd Ed., Elsevier, pp. 189-214 (2003).

* cited by examiner

*Primary Examiner* — Janet Andres
*Assistant Examiner* — Timothy R Rozof
(74) *Attorney, Agent, or Firm* — Samuel B. Rollins

(57) ABSTRACT

The present invention is directed to substituted isoquinoline derivatives, pharmaceutically acceptable salts thereof, and tautomers of such compounds or salts, that inhibit β-site amyloid precursor protein-cleaving enzyme (BACE) and that may be useful in the treatment of diseases in which BACE is involved, such as Alzheimer's disease. The invention is also directed to pharmaceutical compositions comprising these compounds and the use of these compounds and compositions in the treatment of such diseases in which BACE is involved.

17 Claims, No Drawings

SUBSTITUTED ISOQUINOLINE DERIVATIVES, PHARMACEUTICAL COMPOSITIONS, AND METHODS OF USE AS BETA-SECRETASE INHIBITORS

CROSS-REFERENCE TO RELATED APPLICATION

This application is a continuation of international application No. PCT/US2010/031743, filed Apr. 20, 2010, which claims the benefit of priority of U.S. Provisional Patent Application No. 61/173,176, filed Apr. 27, 2009. Each of the aforementioned applications is incorporated by reference in their entirety as though fully set forth herein.

FIELD OF INVENTION

The present invention relates to substituted isoquinoline derivatives useful as inhibitors of β-secretase, the β-site amyloid precursor protein-cleaving enzyme (BACE).

BACKGROUND

Alzheimer's disease is characterized by the abnormal deposition of β-amyloid (Aβ) in the brain in the form of extra-cellular plaques and intra-cellular neurofibrillary tangles. The rate of amyloid accumulation is a combination of the rates of Aβ formation, aggregation, and egress from the brain. It is generally accepted that the main constituent of amyloid plaques is the 4 kD amyloid protein (βA4, also referred to as Aβ, β-protein and βAP) which is a proteolytic product of a precursor protein of much larger size.

Amyloid precursor protein (APP) is a 695-770 amino acid glycoprotein, expressed in the neurons and glial cells in peripheral tissues. APP has a receptor-like structure with a large ectodomain, a membrane spanning region, and a short cytoplasmic tail. Aβ is a 39-42 amino acid peptide, constitutes part of the ectodomain of APP, and extends partly to the transmembrane domain of APP.

At least two secretory mechanisms exist which release APP from the membrane and generate soluble, truncated forms of APP (sAPP). Proteases that release APP and its fragments from the membrane are termed "secretases." Most sAPP is released by a putative α-secretase that cleaves within the Aβ protein to release sAPPα and precludes the release of intact Aβ. A smaller portion of sAPP is released by a β-secretase that cleaves near the $NH_2$-terminus of APP and produces COOH-terminal fragments (CTFs) which contain the complete Aβ domain.

Thus, the activity of β-secretase or β-site amyloid precursor protein-cleaving enzyme ("BACE") leads to the abnormal cleavage of APP, production of Aβ, and accumulation of β-amyloid plaques in the brain, which is characteristic of Alzheimer's disease. In addition, the processing of APP by β-secretase is thought to be the rate-determining step in Aβ production. Therefore, therapeutic agents that can inhibit BACE may be useful for the treatment of Alzheimer's disease.

The compounds of the present invention may be useful for treating Alzheimer's disease by inhibiting the activity of the BACE, thus preventing or reducing the rate of formation of insoluble Aβ.

BRIEF SUMMARY OF THE INVENTION

The present invention is directed to substituted isoquinoline derivatives that inhibit the β-site amyloid precursor protein-cleaving enzyme (BACE) and that therefore may be useful in the treatment of diseases in which BACE is involved, such as Alzheimer's disease. The invention is also directed to pharmaceutical compositions comprising substituted isoquinoline derivatives and the use of these compounds and pharmaceutical compositions in the treatment of diseases in which BACE is involved.

In one aspect, the present invention provides compounds of Formula (I), pharmaceutically acceptable salts thereof, and tautomers of said compounds or salts, where the identity of individual substituents is set forth in greater detail below.

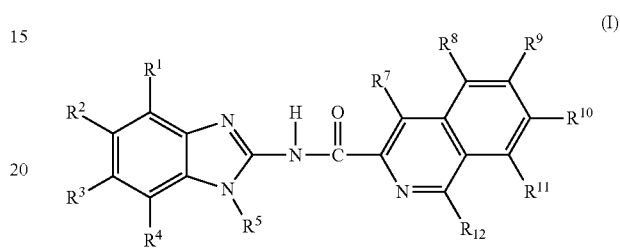

In another aspect, the present invention provides methods for the preparation of compounds of Formula (I), pharmaceutically acceptable salts thereof, and tautomers of said compounds or salts.

In another aspect, the present invention provides pharmaceutical compositions comprising a compound of Formula (I), a pharmaceutically acceptable salt thereof, or a tautomer of said compound or salt. In one embodiment, the pharmaceutical composition comprises a compound of Formula (I), a pharmaceutically acceptable salt thereof, or a tautomer of said compound or salt, and a pharmaceutically acceptable carrier, excipient, diluent, or mixture thereof. In another aspect, the present invention provides a method for the preparation of a pharmaceutical composition comprising a compound of Formula (I), a pharmaceutically acceptable salt thereof, or a tautomer of said compound or salt.

In another aspect, the present invention provides methods of treatment comprising administering a compound of Formula (I), a pharmaceutically acceptable salt thereof, or a tautomer of said compound or salt, or a pharmaceutical composition comprising a compound of Formula (I), a pharmaceutically acceptable salt thereof, or a tautomer of said compound or salt, to a subject who has a disease, disorder, or condition.

In another aspect, the present invention provides methods of treatment comprising administering a compound of Formula (I), a pharmaceutically acceptable salt thereof, or a tautomer of said compound or salt, or a pharmaceutical composition comprising a compound of Formula (I), a pharmaceutically acceptable salt thereof, or a tautomer of said compound or salt to a subject having a disease, disorder, or condition or a subject at risk for having a disease, disorder, or condition, wherein the disease, disorder, or condition is selected from the group consisting of: Alzheimer's disease, mild cognitive impairment, dementia of the Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases.

Additional features of the present invention are described hereinafter.

BRIEF DESCRIPTION OF DRAWINGS

Not applicable.

DETAILED DESCRIPTION

The following definitions are meant to clarify the terms defined. If a particular term used herein is not specifically defined, the term should not be considered to be indefinite. Rather, such undefined terms are to be construed in accordance with their plain and ordinary meaning to skilled artisans in a field of art to which the invention is directed.

As used herein the term "alkyl" refers to a saturated straight or branched chain hydrocarbon having one to twelve carbon atoms, which may be optionally substituted, as herein further described, with multiple degrees of substitution being allowed. Examples of "alkyl" as used herein include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl.

As used throughout this specification, the number carbon atoms in an alkyl group will be represented by the phrase "$C_{x-y}$ alkyl," which refers to an alkyl group, as herein defined, containing from x to y, inclusive, carbon atoms. Thus, $C_{1-6}$ alkyl represents an alkyl chain having from 1 to 6 carbons as described above, and for example, includes, but is not limited to, methyl, ethyl, n-propyl, isopropyl, isobutyl, n-butyl, sec-butyl, tert-butyl, isopentyl, n-pentyl, neopentyl, and n-hexyl. Furthermore, the term "lower alkyl," as used herein, refers to an alkyl group, as herein defined, having from one to six carbon atoms, inclusive.

As used herein, the term "alkylene" refers to a saturated straight or branched chain divalent hydrocarbon radical having from one to ten carbon atoms, which may be optionally substituted as herein further described, with multiple degrees of substitution being allowed. Examples of "alkylene" as used herein include, but are not limited to, methylene, ethylene, n-propylene, 1-methylethylene, 2-methylethylene, dimethylmethylene, n-butylene, 1-methyl-n-propylene, and 2-methyl-n-propylene.

As used throughout this specification, the number of carbon atoms in an alkylene group will be represented by the phrase "$C_{x-y}$ alkylene," which refers to an alkylene group, as herein defined, containing from x to y, inclusive, carbon atoms. Thus, $C_{1-4}$ alkylene represents an alkylene chain having from 1 to 4 carbons as described above, and for example, includes, but is not limited to, methylene, ethylene, n-propylene, 1-methylethylene, 2-methylethylene, dimethylmethylene, n-butylene, 1-methyl-n-propylene, and 2-methyl-n-propylene.

As used herein, the term "alkenylene" refers to a straight or branched chain divalent hydrocarbon radical having from two to ten carbon atoms, and containing one or more carbon-to-carbon double bond, which may be optionally substituted as herein further described, with multiple degrees of substitution being allowed. Examples of "alkenylene" as used herein include, but are not limited to, vinylene, allylene, and 2-propenylene.

As used throughout this specification, the number of carbon atoms in an alkenylene group will be represented by the phrase "$C_{x-y}$ alkenylene," which refers to an alkenylene group, as herein defined, containing from x to y, inclusive, carbon atoms. Thus, $C_{1-4}$ alkenylene represents an alkenylene chain having from 1 to 4 carbons as described above, and for example, includes, but is not limited to, vinylene, allylene, and 2-propenylene.

As used herein, the term "alkynylene" refers to a straight or branched chain divalent hydrocarbon radical having from one to ten carbon atoms, and containing at least one carbon-to-carbon triple bond, which may be optionally substituted as herein further described, with multiple degrees of substitution being allowed. Examples of "alkynylene" as used herein include, but are not limited to, ethynylene and propynylene.

As used throughout this specification, the number of carbon atoms in an alkynylene group will be represented by the phrase "$C_{x-y}$ alkynylene," which refers to an alkynylene group, as herein defined, containing from x to y, inclusive, carbon atoms. Thus, $C_{1-4}$ alkynylene represents an alkynylene chain having from 1 to 4 carbons as described above, and for example, includes, but is not limited to, ethynylene and propynylene.

As used herein, the term "cycloalkyl" refers to a three- to twelve-membered, cyclic hydrocarbon ring, which may be optionally substituted as herein further described, with multiple degrees of substitution being allowed. The term "cycloalkyl," as used herein, does not include ring systems which contain any aromatic rings, but does include ring systems that have one or more degrees of unsaturation. Examples of "cycloalkyl" groups as used herein include, but are not limited to, cyclopropyl, cyclobutyl, cyclopentyl, cyclohexyl, cycloheptyl, 1-norbornyl, 2-norbornyl, 7-norbornyl, 1-adamantyl, and 2-adamantyl.

As used throughout this specification, the number of carbon atoms in a cycloalkyl group will be represented by the phrase "$C_{x-y}$ cycloalkyl," which refers to a cycloalkyl group, as herein defined, containing from x to y, inclusive, carbon atoms. Similar terminology will apply for other terms and ranges as well. Thus, $C_{3-10}$ cycloalkyl represents a cycloalkyl group having from 3 to 10 carbons as described above, and for example, includes, but is not limited to, cyclopropyl, cyclobutyl, cyclopentyl, cyclohexyl, cycloheptyl, 1-norbornyl, 2-norbornyl, 7-norbornyl, 1-adamantyl, and 2-adamantyl.

As used herein, the term "heterocycle" or "heterocyclyl" refers to a mono-, bi-, or tricyclic ring system containing one or more heteroatoms. Such "heterocycle" or "heterocyclyl" groups may be optionally substituted as herein further described, with multiple degrees of substitution being allowed. The terms "heterocycle" or "heterocyclyl," as used herein, do not include ring systems which contain any aromatic rings, but do include ring systems that have one or more degrees of unsaturation. Examples of heteroatoms include nitrogen, oxygen, or sulfur atoms, including N-oxides, sulfur oxides, and sulfur dioxides. Carbon atoms in the ring system can also be optionally oxidized to form heterocyclic rings such as, 2-oxo-pyrrolidin-1-yl or 2-oxo-piperidin-1-yl. Typically, the ring is three- to twelve-membered. Such rings may be optionally fused to one or more of another heterocyclic ring(s) or cycloalkyl ring(s). Examples of "heterocycle" or "heterocyclyl" groups, as used herein, include, but are not limited to, tetrahydrofuran, tetrahydropyran, 1,4-dioxane, 1,3-dioxane, piperidine, pyrrolidine, morpholine, tetrahydrothiopyran, and tetrahydrothiophene, where attachment can occur at any point on said rings, as long as attachment is chemically feasible. Thus, for example, "morpholine" can refer to morpholin-2-yl, morpholin-3-yl, and morpholin-4-yl.

As used herein, when "heterocycle" or "heterocyclyl" is recited as a possible substituent, the "heterocycle" or "heterocyclyl" group can attach through either a carbon atom or any heteroatom, to the extent that attachment at that point is chemically feasible. For example, "heterocyclyl" would include pyrrolidin-1-yl, pyrrolidin-2-yl, and pyrrolidin-3-yl. When "heterocycle" or "heterocyclyl" groups contain a nitrogen atom in the ring, attachment through the nitrogen atom can alternatively be indicated by using an "-ino" suffix with the ring name. For example, pyrrolidino refers to pyrrolidin-1-yl.

As used herein the term "halogen" refers to fluorine, chlorine, bromine, or iodine.

As used herein the term "haloalkyl" refers to an alkyl group, as defined herein, that is substituted one or more times with halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include groups such as —$CF_3$, —$CH_2$—$CF_3$, and —$CF_2Cl$.

As used herein, the term "aryl" refers to a six- to ten-membered cyclic, aromatic hydrocarbon, which may be optionally substituted as herein further described, with multiple degrees of substitution being allowed. Examples of "aryl" groups as used herein include, but are not limited to, phenyl and naphthyl. As used herein, the term "aryl" also includes ring systems in which a phenyl or naphthyl group is optionally fused with one to three non-aromatic, saturated or unsaturated, carbocyclic rings. For example, "aryl" would include ring systems such as indene, with attachment possible to either the aromatic or the non-aromatic ring(s).

As used herein, the term "heteroaryl" refers to a five- to fourteen-membered optionally substituted mono- or polycyclic ring system, which contains at least one aromatic ring and also contains one or more heteroatoms. Such "heteroaryl" groups may be optionally substituted as herein further described, with multiple degrees of substitution being allowed. In a polycyclic "heteroaryl" group that contains at least one aromatic ring and at least one non-aromatic ring, the aromatic ring(s) need not contain a heteroatom. Thus, for example, "heteroaryl," as used herein, would include indolinyl. Further, the point of attachment may be to any ring within the ring system without regard to whether the ring containing the attachment point is aromatic or contains a heteroatom. Thus, for example, "heteroaryl," as used herein, would include indolin-1-yl, indolin-3-yl, and indolin-5-yl. Examples of heteroatoms include nitrogen, oxygen, or sulfur atoms, including N-oxides, sulfur oxides, and sulfur dioxides, where feasible. Examples of "heteroaryl" groups, as used herein include, but are not limited to, furyl, thiophenyl, pyrrolyl, oxazolyl, thiazolyl, imidazolyl, isoxazolyl, isothiazolyl, 1,2,4-triazolyl, pyrazolyl, pyridinyl, pyridazinyl, pyrimidinyl, indolyl, isoindolyl, benzo[b]thiophenyl, benzimidazolyl, benzothiazolyl, pteridinyl, and phenazinyl, where attachment can occur at any point on said rings, as long as attachment is chemically feasible. Thus, for example, "thiazolyl" refers to thiazol-2-yl, thiazol-4-yl, and thiaz-5-yl.

As used herein, when "heteroaryl" is recited as a possible substituent, the "heteroaryl" group can attach through either a carbon atom or any heteroatom, to the extent that attachment at that point is chemically feasible.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a substituent group is recited without an asterisk or a dash, then its attachment point is the attachment point that skilled artisans would generally associate with that group. For example, "methyl" is —$CH_3$, as that conforms to the generally understood meaning of what a methyl group is.

When any variable occurs more than one time in any one constituent (e.g., $R^a$), or multiple constituents, its definition on each occurrence is independent of its definition on every other occurrence.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, the term "optionally" means that the subsequently described event(s) may or may not occur.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of: delaying the progress of a disease, disorder, or condition; controlling a disease, disorder, or condition; delaying the onset of a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms.

As used herein, "subject" refers to any mammal such as, but not limited to, humans, horses, cows, sheep, pigs, mice, rats, dogs, cats, and primates such as chimpanzees, gorillas, and rhesus monkeys. In an embodiment, the "subject" is a human. In another embodiment, the "subject" is a human who exhibits one or more symptoms characteristic of a disease, disorder, or condition. In another embodiment, the "subject" is a human who has a disease, disorder, or condition in which BACE is involved. The term "subject" does not require one to have any particular status with respect to a hospital, clinic, or research facility (e.g., as an admitted patient, a study participant, or the like).

As used herein, the term "compound" includes free acids, free bases, and salts thereof. Thus, phrases such as "the compound of embodiment 1" or "the compound of claim 1" are intended to refer to any free acids, free bases, and salts thereof that are encompassed by embodiment 1 or claim 1.

As used herein, "substituted imidazo[1,2-a]pyridines derivatives" refers to derivatives of 2-imidazo[1,2-a]pyridine carboxylic acid benzimidazol-2-yl amide or 3-imidazo[1,2-a]pyridine carboxylic acid benzimidazol-2-yl amide represented by Formula (I), as described in detail below.

As used herein, the term "pharmaceutical composition" is used to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

As used herein, the term "tautomer," used in reference to compounds or salts of the invention, refers to tautomers that can form with respect to substituted benzimidazole groups, as shown below.

lation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

As used herein the terms "pharmaceutically acceptable carrier", "pharmaceutically acceptable diluent", and "pharmaceutically acceptable excipient" means the carrier, diluent or excipient must be compatible with the other ingredients of the formulation and not deleterious to the recipient thereof.

Also included within the scope of the invention are the individual enantiomers of the compounds represented by Formula (I), pharmaceutically acceptable salts thereof, or tautomers of said compounds or salts, as well as any wholly or partially racemic mixtures thereof. The invention also covers the individual enantiomers of the compounds represented by Formula (I), pharmaceutically acceptable salts thereof, or tautomers of said compounds or salts, as well as mixtures with diastereoisomers thereof in which one or more stereocenters are inverted. Unless otherwise stated, structures depicted herein are also meant to include compounds which differ only in the presence of one or more isotopically

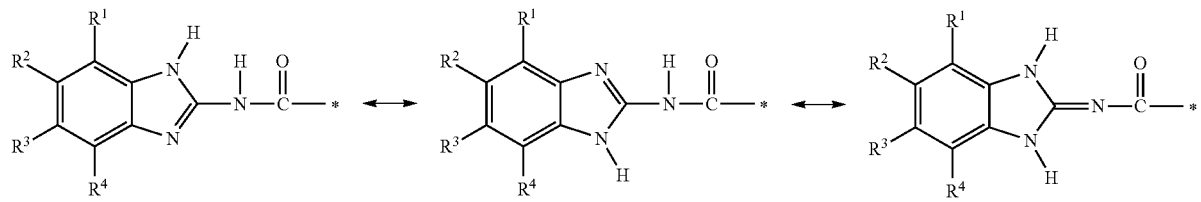

The present invention includes all such tautomers and methods of making and using the same. Throughout this specification, whenever a chemical formula (generic or otherwise) discloses a compound having a 1H-benzimidazole moiety that is unsubstituted at the 1 position (as illustrated in the far left-hand structure shown immediately above), that chemical formula also implicitly discloses compounds that are otherwise identical except that the benzimidazole moiety undergoes tautomerization to form either of the other two benzimidazole tautomers shown immediately above. Thus, the phrase "a tautomer of a compound of Formula (I)" refers to compounds of Formula (I) where the $R^5$ group of Formula (I) is hydrogen, and where said tautomer is related to a compound of Formula (I) according to the tautomeric relationship described immediately above.

As used herein, the term "BACE inhibitor" or "inhibitor of BACE" is used to signify a compound having a structure, as defined herein, which is capable of interacting with BACE and inhibiting its enzymatic activity. Inhibiting BACE enzymatic activity means reducing the ability of BACE to cleave a peptide or protein. The peptide or protein may be APP, and a BACE inhibitor may reduce the ability of BACE to cleave APP near the $NH_2$ terminus of APP and produce COOH-terminal fragments (CTFs) that contain the complete Aβ domain. In various embodiments, such reduction of BACE activity is at least about 50%, at least about 75%, at least about 90%, at least about 95%, or at least about 99%. In various embodiments, the concentration of BACE inhibitor required to reduce a BACE's enzymatic activity is less than about 30 µM, less than about 10 µM, or less than about 1 µM.

As used herein, the term "pharmaceutical composition" is used to denote a composition that may be administered to a mammalian host, e.g., orally, topically, parenterally, by inhaenriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

In several aspects, the present invention relates to substituted isoquinoline derivatives, pharmaceutical compositions comprising substituted isoquinoline derivatives, methods of making substituted isoquinoline derivatives, methods of making pharmaceutical compositions comprising substituted isoquinoline derivatives, and methods of using substituted isoquinoline derivatives or pharmaceutical compositions comprising substituted isoquinoline derivatives, particularly for the treatment of diseases, disorders, or conditions that may be related to the enzymatic activity of BACE, such as Alzheimer's disease.

In a first aspect, the present invention provides substituted isoquinoline derivatives, pharmaceutically acceptable salts thereof, and tautoers of said compounds or salts. Such compounds, salts, or tautomers thereof are useful in the reduction of the proteolytic activity of BACE, as discussed in more detail below.

In a first embodiment (i.e., embodiment 1), the present invention provides a compound of Formula (I), a tautomer of a compound of Formula (I), or a pharmaceutically acceptable salt of either of the foregoing:

(I)

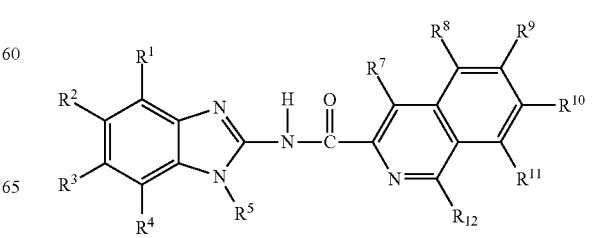

wherein
$R^7$, $R^8$, $R^9$, $R^{10}$, $R^{11}$, and $R^{12}$ are each independently selected from the group consisting of:
a) —H,
b) -halo,
c) $R^a$,
d) -$J^1$-$R^b$,
e) -alkylene-$J^2$-$R^b$,
f) -$J^1$-alkylene-$J^2$-$R^b$,
g) —N($R^d$)($R^e$),
h) -alkylene-N($R^d$)($R^e$),
i) -$J^1$-alkylene-N($R^d$)($R^e$),
j) —N(-alkylene-$R^f$)(-alkylene-$R^g$),
k) —C(O)$R^d$,
l) —CO$_2$—$R^d$,
m) —SO$_2$-alkyl,
n) —SO$_2$—O$R^d$,
o) —SO$_2$—N($R^d$)($R^e$),
p) -$J^2$-alkylene-C(O)$R^d$,
q) -$J^2$-alkylene-CO$_2R^d$,
r) -$J^2$-alkylene-C(O)N($R^d$)($R^e$),
s) -$J^2$-alkylene-SO$_2$-alkyl,
t) -$J^2$-alkylene-SO$_2$—O$R^d$, and
u) -$J^2$-alkylene-SO$_2$—N($R^d$)($R^e$),
wherein the alkylene groups are optionally substituted with one or more substituents independently selected from $R^c$, and
$J^1$ is selected from the group consisting of: —O—, —NH—, and —S—,
$J^2$ is selected from the group consisting of: direct bond, —O—, —NH—, and —S—;
$R^1$ and $R^4$ are independently selected from the group consisting of:
a) -hydrogen,
b) -halo,
c) -alkyl,
d) -haloalkyl,
e) —O-alkyl, and
f) —O-haloalkyl;
$R^2$ and $R^3$ are independently selected from the group consisting of:
a) -hydrogen,
b) -halo,
c) -alkyl,
d) -haloalkyl,
e) —O-alkyl,
f) —O-haloalkyl, and
g) -$L^2$-$D^2$-$G^2$,
wherein at least one of $R^2$ and $R^3$ is -$L^2$-$D^2$-$G^2$, and wherein
$L^2$ is selected from the group consisting of: direct bond, —O—, —NH—, and —N($R^6$)—;
wherein $R^6$ is -$D^3$-$G^3$, wherein
$D^3$ is selected from the group consisting of: a direct bond, -alkylene-, and -alkenylene-; and
$G^3$ is selected from the group consisting of: -phenyl and -cycloalkyl, wherein the phenyl and cycloalkyl groups are optionally substituted with one or more substituents independently selected from the group consisting of: -halo, -alkyl, -haloalkyl, —OH, —NH$_2$, -phenyl, -cycloalkyl, -alkylene-phenyl, -alkylene-cycloalkyl, —O-alkyl, —O-haloalkyl, —O-phenyl, —O-cycloalkyl, —O-alkylene-phenyl, —O-alkylene-cycloalkyl, —C(O)alkyl, and —C(O)haloalkyl;
$D^2$ is selected from the group consisting of: a direct bond, -alkylene-, and -alkenylene-; and $G^2$ is selected from the group consisting of: -phenyl and -cycloalkyl, wherein the phenyl and cycloalkyl groups are optionally substituted with one or more substituents independently selected from the group consisting of: -halo, -alkyl, -haloalkyl, —OH, —NH$_2$, -phenyl, -cycloalkyl, -alkylene-phenyl, -alkylene-cycloalkyl, —O-alkyl, —O-haloalkyl, —O-phenyl, —O-cycloalkyl, —O-alkylene-phenyl, —O-alkylene-cycloalkyl, —C(O)alkyl, and —C(O)haloalkyl;
$R^5$ is selected from the group consisting of: hydrogen, -haloalkyl, -alkyl, -alkylene-$J^3$-$R^d$, -alkylene-N($R^d$)($R^e$), -alkylene-C(O)$R^d$, -alkylene-CO$_2R^d$, -alkylene-C(O)N($R^d$)($R^e$), -alkylene-SO$_2$-alkyl, -alkylene-SO$_2$—O$R^d$, and -alkylene-SO$_2$—N($R^d$)($R^e$), wherein $J^3$ is selected from the group consisting of: direct bond, —O—, —NH—, and —S—;
$R^a$ is selected from the group consisting of: alkyl, haloalkyl, phenyl, cycloalkyl, piperidine-4-yl, piperidine-3-yl, and pyrrolidine-3-yl, wherein the alkyl, phenyl, cycloalkyl, piperidine-4-yl, piperidine-3-yl, and pyrrolidine-3-yl groups are optionally substituted with one or more substituents independently selected from $R^c$;
$R^b$ is selected from the group consisting of: hydrogen, alkyl, haloalkyl, phenyl, cycloalkyl, piperidine-4-yl, piperidine-3-yl, and pyrrolidine-3-yl, wherein the alkyl, phenyl, cycloalkyl, piperidine-4-yl, piperidine-3-yl, and pyrrolidine-3-yl groups are optionally substituted with one or more substituents independently selected from $R^c$;
$R^c$ is selected from the group consisting of: halo, haloalkyl, alkyl, cycloalkyl, phenyl, —OH, —NH$_2$, —N(H)alkyl, —N(alkyl)$_2$, —O-haloalkyl, —O-alkyl, —O-cycloalkyl, —O-phenyl, and —O-alkylene-phenyl;
$R^d$ and $R^e$ are independently selected from the group consisting of: hydrogen, alkyl, phenyl, and cycloalkyl, wherein the alkyl, phenyl, and cycloalkyl groups are optionally substituted with one or more substituents independently selected from $R^c$, or $R^d$ and $R^e$ are taken together with the atom to which they are attached to form a ring, wherein $R^d$ and $R^e$ together have the formula —(C$R^fR^g$)$_s$—$X^1$—(C$R^fR^g$)$_t$—, wherein s and t are independently 1, 2, or 3, and the sum of s and t is equal to 3 or 4, and $X^1$ is selected from the group consisting of: direct bond, —CH$_2$—, —O—, —S—, and —N$R^{13}$—, wherein $R^{13}$ is hydrogen or alkyl; and
$R^f$ and $R^g$ are independently selected from the group consisting of: hydrogen, halo, haloalkyl, alkyl, cycloalkyl, phenyl, —OH, —NH$_2$, —N(H)alkyl, —N(alkyl)$_2$, —O-haloalkyl, —O-alkyl, —O-cycloalkyl, —O-phenyl, and —O-alkylene-phenyl, wherein the alkyl, phenyl, cycloalkyl groups are optionally substituted with one or more substituents independently selected from $R^c$.

Embodiment 2: A compound according to embodiment 1, wherein $R^{13}$ is hydrogen.

Embodiment 3: A compound according to embodiment 1 or 2, wherein $R^5$ is hydrogen.

Embodiment 4: A compound according to embodiment 1 or 2, wherein $R^5$ is methyl.

Embodiment 5: A compound according to embodiment 1 or 2, wherein $R^5$ is -alkylene-$J^3$-$R^d$.

Embodiment 6: A compound according to embodiment 5, wherein $R^5$ is -alkylene-O—$R^d$.

Embodiment 7: A compound according to embodiment 1 or 2, wherein $R^5$ is -alkylene-N($R^d$)($R^e$).

Embodiment 8: A compound according to embodiment 1 or 2, wherein $R^5$ is -alkylene-C(O)$R^d$.

Embodiment 9: A compound according to embodiment 1 or 2, wherein $R^5$ is -alkylene-CO$_2R^d$.

Embodiment 10: A compound according to embodiment 1 or 2, wherein $R^5$ is -alkylene-C(O)N($R^d$)($R^e$).

Embodiment 11: A compound according to embodiment 1 or 2, wherein $R^5$ is -alkylene-SO$_2$-alkyl.

Embodiment 12: A compound according to embodiment 1 or 2, wherein $R^5$ is -alkylene-SO$_2$—OR$^d$.

Embodiment 13: A compound according to embodiment 1 or 2, wherein $R^5$ is -alkylene-SO$_2$—N($R^d$)($R^e$).

Embodiment 14: A compound according to any one of embodiments 1 through 13, wherein one of $R^7$, $R^8$, $R^9$, $R^{10}$, $R^{11}$, and $R^{12}$ is not hydrogen.

Embodiment 15: A compound according to any one of embodiments 1 through 13, wherein two of $R^7$, $R^8$, $R^9$, $R^{10}$, $R^{11}$, and $R^{12}$ are not hydrogen.

Embodiment 16: A compound according to any one of embodiments 1 through 13, wherein $R^7$, $R^8$, $R^9$, $R^{10}$, $R^{11}$, and $R^{12}$ are all hydrogen.

Embodiment 17: A compound according to any one of embodiments 1 through 15, wherein $R^7$, $R^8$, $R^9$, $R^{10}$, $R^{11}$, and $R^{12}$ are independently selected from the group consisting of: —H, -halo, and $R^a$.

Embodiment 18: A compound according to any one of embodiments 1 through 15, wherein $R^7$, $R^8$, $R^9$, $R^{10}$, $R^{11}$, and $R^{12}$ are independently selected from the group consisting of:
a) —H,
b) -halo,
c) —C$_{1-4}$ alkyl,
d) —C$_{1-4}$ haloalkyl,
e) —O—C$_{1-4}$ alkyl,
f) —O—C$_{1-4}$ haloalkyl,
g) —O—C$_{1-4}$ alkylene-phenyl,
h) —NH—C$_{1-4}$ alkyl,
i) —NH—C$_{1-2}$ alkylene-phenyl,
j) —N—(C$_{1-4}$ alkyl)$_2$, and
k) —N—(C$_{1-2}$ alkylene-phenyl)$_2$.

Embodiment 19: A compound according to any one of embodiments 1 through 15, wherein $R^7$, $R^8$, $R^9$, $R^{10}$, $R^{11}$, and $R^{12}$ are independently selected from the group consisting of: —H, -halo, —C$_{1-4}$ alkyl, —C$_{1-4}$ haloalkyl, —O—C$_{1-4}$ alkyl, —O—C$_{1-4}$ haloalkyl, -J$^1$-R$^b$, -alkylene-J$^2$-R$^b$, and -J$^1$-alkylene-J$^2$-R$^b$.

Embodiment 20: A compound according to any one of embodiments 1 through 15, wherein $R^7$, $R^8$, $R^9$, $R^{10}$, $R^{11}$, and $R^{12}$ are independently selected from the group consisting of: —H, -halo, —C$_{1-4}$ alkyl, —C$_{1-4}$ haloalkyl, —O—C$_{1-4}$ alkyl, —O—C$_{1-4}$ haloalkyl, —N($R^d$)($R^e$), -alkylene-N($R^d$)($R^e$), and -J$^1$-alkylene-N($R^d$)($R^e$).

Embodiment 21: A compound according to any one of embodiments 1 through 15, wherein $R^7$, $R^8$, $R^9$, $R^{10}$, $R^{11}$, and $R^{12}$ are independently selected from the group consisting of: —H, -halo, —C$_{1-4}$ alkyl, —C$_{1-4}$ haloalkyl, —O—C$_{1-4}$ alkyl, —O—C$_{1-4}$ haloalkyl, —C(O)R$^d$, —CO$_2$—R$^d$, —SO$_2$-alkyl, —SO$_2$—OR$^d$, and —SO$_2$—N($R^d$)($R^e$).

Embodiment 22: A compound according to any one of embodiments 1 through 15, wherein $R^7$, $R^8$, $R^9$, $R^{10}$, $R^{11}$, and $R^{12}$ are independently selected from the group consisting of: —H, -halo, —C$_{1-4}$ alkyl, —C$_{1-4}$ haloalkyl, —O—C$_{1-4}$ alkyl, —O—C$_{1-4}$ haloalkyl, -J$^2$-alkylene-C(O)R$^d$, -J$^2$-alkylene-CO$_2$R$^d$, -J$^2$-alkylene-C(O)N($R^d$)($R^e$), -J$^2$-alkylene-SO$_2$-alkyl, -J$^2$-alkylene-SO$_2$—OR$^d$, and -J$^2$-alkylene-SO$_2$—N($R^d$)($R^e$).

Embodiment 23: A compound according to any one of embodiments 1 through 22, wherein $R^1$ and $R^4$ are independently selected from the group consisting of: -hydrogen, -halo, -alkyl, -haloalkyl, —O-alkyl, and —O-haloalkyl.

Embodiment 24: A compound according to embodiment 23, wherein at least one of $R^1$ and $R^4$ is hydrogen.

Embodiment 25: A compound according to embodiment 23, wherein $R^1$ and $R^4$ are hydrogen.

Embodiment 26: A compound according to any one of embodiments 1 to 22, wherein $R^1$ and $R^4$ are hydrogen, one of $R^2$ and $R^3$ is hydrogen, and the other of $R^2$ and $R^3$ is the group -L$^2$-D$^2$-G$^2$.

Embodiment 27: A compound according to any one of embodiments 1 to 26, wherein one of $R^2$ and $R^3$ is -L$^2$-D$^2$-G$^2$, and wherein L$^2$ is a direct bond.

Embodiment 28: A compound according to embodiment 27, wherein D$^2$ is a direct bond.

Embodiment 29: A compound according to embodiment 27, wherein D$^2$ is —C$_{1-3}$ alkylene-.

Embodiment 30: A compound according to embodiment 27, wherein D$^2$ is —C(H)=C(H)—.

Embodiment 31: A compound according to any one of embodiments 27 to 30, wherein G$^2$ is phenyl, wherein the phenyl group is optionally substituted as described in embodiment 1.

Embodiment 32: A compound according to embodiment 31, wherein G$^2$ is -phenyl, and wherein the phenyl group is unsubstituted.

Embodiment 33: A compound according to embodiment 31, wherein G$^2$ is -phenyl, wherein the phenyl group is substituted with one or more substituents independently selected from the group consisting of: halo, -alkyl, -haloalkyl, —O-alkyl, —O-haloalkyl, and —C(O)-haloalkyl.

Embodiment 34: A compound according to embodiment 31, wherein G$^2$ is -phenyl, wherein the phenyl group is substituted with one or more substituents independently selected from the group consisting of: —F, —Cl, —C$_{1-3}$ alkyl, —CF$_3$, —O—C$_{1-3}$ alkyl, —O—CF$_3$, —CH$_2$—CF$_3$, and —C(O)—CF$_3$.

Embodiment 35: A compound according to any one of embodiments 27 to 30, wherein G$^2$ is -cycloalkyl, wherein the cycloalkyl group is optionally substituted as described in embodiment 1.

Embodiment 36: A compound according to embodiment 35, wherein G$^2$ is -cycloalkyl, wherein the cycloalkyl group is unsubstituted.

Embodiment 37: A compound according to embodiment 35, wherein G$^2$ is -cycloalkyl, wherein the cycloalkyl group is substituted with one or more substituents independently selected from the group consisting of: halo, -alkyl, -haloalkyl, —O-alkyl, —O-haloalkyl, and —C(O)-haloalkyl.

Embodiment 38: A compound according to embodiment 35, wherein G$^2$ is -cycloalkyl, wherein the cycloalkyl group is substituted with one or more substituents independently selected from the group consisting of: —F, —Cl, —C$_{1-3}$ alkyl, —CF$_3$, —O—C$_{1-3}$ alkyl, —O—CF$_3$, —CH$_2$—CF$_3$, and —C(O)—CF$_3$.

Embodiment 39: A compound according to any one of embodiments 35 through 38, wherein G$^2$ is cyclopentyl or cyclohexyl, each of which is optionally substituted as described in embodiments 35 through 38.

Embodiment 40: A compound according to any one of embodiments 1 to 26, wherein one of $R^2$ and $R^3$ is -L$^2$-D$^2$-G$^2$, wherein L$^2$ is —O— and D$^2$ is a direct bond or -alkylene-.

Embodiment 41: A compound according to embodiment 40, wherein D$^2$ is —CH$_2$— or —CH$_2$—CH$_2$—.

Embodiment 42: A compound according to embodiment 40 or 41, wherein $G^2$ is phenyl, wherein the phenyl group is optionally substituted as described in embodiment 1.

Embodiment 43: A compound according to embodiment 42, wherein $G^2$ is -phenyl, wherein the phenyl group is unsubstituted.

Embodiment 44: A compound according to embodiment 42, wherein $G^2$ is -phenyl, wherein the phenyl group is substituted with one or more substituents independently selected from the group consisting of: halo, -alkyl, -haloalkyl, —O-alkyl, —O-haloalkyl, and —C(O)-haloalkyl.

Embodiment 45: A compound according to embodiment 42, wherein $G^2$ is -phenyl, wherein the phenyl group is substituted with one or more substituents independently selected from the group consisting of: —F, —Cl, —$C_{1-3}$ alkyl, —$CF_3$, —O—$C_{1-3}$ alkyl, —O—$CF_3$, —$CH_2$—$CF_3$, and —C(O)—$CF_3$.

Embodiment 46: A compound according to embodiment 40 or 41, wherein $G^2$ is -cycloalkyl, wherein the cycloalkyl group is optionally substituted as described in embodiment 1.

Embodiment 47: A compound according to embodiment 46, wherein $G^2$ is -cycloalkyl, wherein the cycloalkyl group is unsubstituted.

Embodiment 48: A compound according to embodiment 46, wherein $G^2$ is -cycloalkyl, wherein the cycloalkyl group is substituted with one or more substituents independently selected from the group consisting of: halo, -alkyl, -haloalkyl, —O-alkyl, —O-haloalkyl, and —C(O)-haloalkyl.

Embodiment 49: A compound according to embodiment 46, wherein $G^2$ is -cycloalkyl, wherein the cycloalkyl group is substituted with one or more substituents independently selected from the group consisting of: —F, —Cl, —$C_{1-3}$ alkyl, —$CF_3$, —O—$CF_3$, —$CH_2$—$CF_3$, and —C(O)—$CF_3$.

Embodiment 50: A compound according to any one of embodiments 46 to 49, wherein $G^2$ is a cyclopentyl or cyclohexyl group, each of which is optionally substituted as described in embodiments 46 through 49.

Embodiment 51: A compound according to any one of embodiments 1 to 26, wherein one of $R^2$ and $R^3$ is -$L^2$-$D^2$-$G^2$, wherein $L^2$ is —NH— or —N($R^6$)— and $D^2$ is a direct bond or -alkylene-.

Embodiment 52: A compound according to embodiment 51, wherein $D^2$ is —$CH_2$— or —$CH_2$—$CH_2$—, and $R^6$ is -$D^3$-$G^3$, wherein $D^3$ is —$CH_2$— or —$CH_2$—$CH_2$—.

Embodiment 53: A compound according to embodiment 51 or 52, wherein $G^2$ and $G^3$ are phenyl, wherein each phenyl group is optionally substituted as described in embodiment 1.

Embodiment 54: A compound according to embodiment 53, wherein $G^2$ and $G^3$ are -phenyl, wherein each phenyl group is unsubstituted.

Embodiment 55: A compound according to embodiment 53, wherein $G^2$ and $G^3$ are -phenyl, wherein each phenyl group is substituted with one or more substituents independently selected from the group consisting of: halo, -alkyl, -haloalkyl, —O-alkyl, —O-haloalkyl, and —C(O)-haloalkyl.

Embodiment 56: A compound according to embodiment 53, wherein $G^2$ and $G^3$ are -phenyl, wherein each phenyl group is substituted with one or more substituents independently selected from the group consisting of: —F, —Cl, —$C_{1-3}$ alkyl, —$CF_3$, —O—$C_{1-3}$ alkyl, —O—$CF_3$, —$CH_2$—$CF_3$, and —C(O)—$CF_3$.

Embodiment 57: A compound according to any one of embodiments 1 to 56, wherein the compound is in its free (non-salted) form.

Embodiment 58: A compound according to any one of embodiments 1 to 56, wherein the compound is in the form of a pharmaceutically acceptable salt.

Embodiment 59: A compound according to any one of embodiments 1 to 58, wherein $R^5$ is hydrogen and the benzimidazole exists in the following tautomeric form:

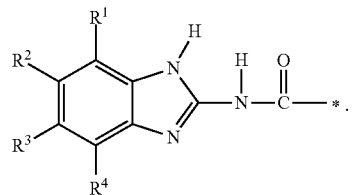

Embodiment 60: A compound according to any one of embodiments 1 to 58, wherein $R^5$ is hydrogen and the benzimidazole exists in the following tautomeric form:

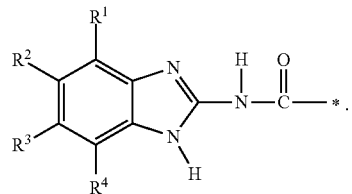

Embodiment 61: A compound according to any one of embodiments 1 to 58, wherein $R^5$ is hydrogen and the benzimidazole exists in the following tautomeric form:

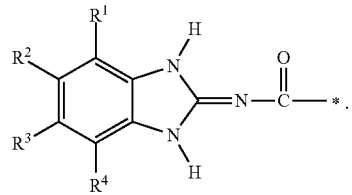

General Experimental Section

The routes below illustrate general methods of synthesizing compounds of Formula (I), tautomers of compounds of Formula (I), and/or pharmaceutically acceptable salts of either of the foregoing. The skilled artisan will appreciate that the compounds of the invention could be made by methods other than those specifically described herein, by adaptation of the methods described herein and/or by adaptation of methods known in the art. In general, compounds of the invention may be prepared in a multi-step synthesis, as shown below. All quantities shown are approximate, and are given solely for illustrative purposes.

The following abbreviations may be used in describing reaction conditions, common reagents, common solvents, or methods of analysis.

| | |
|---|---|
| DCM = | dichloromethane |
| DIEA = | diisopropylethylamine |
| DMF = | N,N'-dimethylformamide |
| DMSO = | dimethylsulfoxide |
| HBTU = | 2-(1H-benzotriazol-1-yl)-1,1,3,3- |

| | |
|---|---|
| | tetramethyluronium hexafluorophosphate |
| HCl = | hydrochloric acid |
| LCMS = LC-MS = LC/MS = | liquid chromatography-mass spectrometry analysis |
| THF = | tetrahydrofuran |
| TLC = | thin layer chromatography |
| rt or RT = | room temperature |
| h = | hour |
| min = | minutes |
| M = | molar concentration |
| N = | normal concentration |

Step 1-A: Synthesis of a substituted 2-aminobenzimidazole. To a mixture of 4-bromo-2-nitroaniline (1 mmol), a boronic acid (1.5 mmol), and Na$_2$CO$_3$ (3 mmol), toluene (10 mL) and water (5 mL) is added. The resulting mixture is purged with nitrogen for 10 minutes. Then, tetrakis(triphenylphosphine)palladium (0.05 mmol) is added, and the reaction mixture is heated at reflux for 4 hours under nitrogen. The reaction mixture is then cooled to room temperature and filtered through Celite, and then is washed with ethyl acetate. The organic layer is separated and dried over sodium sulfate, and then concentrated and purified by column chromatography using a silica gel stationary phase and ethyl acetate in hexanes as an eluent. The purified solution contains a 4-substituted-2-nitroaniline compound.

The 4-substituted-2-nitroaniline compound (1 mmol) is taken up into solution using an ethyl acetate-methanol mixture (about 1:1). To this solution, Pd—C is added, and the resulting mixture is stirred under a hydrogen atmosphere for about 6 hours. Then, the solution is filtered on Celite, washed with methanol, and then concentrated until the characteristic dark-brown color of a diamine is apparent. The diamine compound is taken up into methanol, and CNBr (1 mmol) would be added. The resulting mixture is stirred at room temperature for about 30 minutes. The solution is then concentrated to dryness, and residual methanol is removed by co-evaporating with toluene about 3 times, followed by drying to obtain a substituted 2-aminobenzimidazole derivative as a hydrobromide salt. The reaction scheme below provides an illustration that accompanies this textual description.

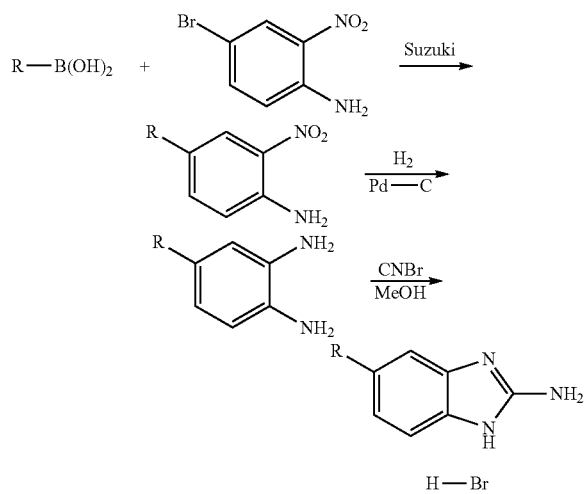

Step 1-B: Alternate synthesis of a substituted 2-aminobenzimidazole. To a mixture of 4-bromo-benzene-1,2-diamine (1 mmol), a boronic acid (1.5 mmol), and Na$_2$CO$_3$ (3 mmol), toluene (10 mL) and water (5 mL) are added. The resulting mixture is purged with nitrogen for 10 minutes. Then, tetrakis(triphenylphosphine)palladium (0.05 mmol) is added, and the mixture is heated at reflux for 4 hours under nitrogen. The reaction mixture is then cooled to room temperature and filtered through Celite, and then is washed with ethyl acetate. The organic layer is separated and dried over sodium sulfate, and then concentrated and purified by column chromatography using a silica gel stationary phase and ethyl acetate in hexanes as an eluent. The purified solution contains a 4-substituted-1,2-diaminophenyl compound. The diamine compound is taken up into methanol, and CNBr (1 mmol) is added. The resulting mixture is stirred at room temperature for about 30 minutes. The solution is then concentrated to dryness, and residual methanol is removed by co-evaporating with toluene about 3 times, followed by drying to obtain a substituted 2-aminobenzimidazole derivative as hydrobromide salt. The reaction scheme below provides an illustration that accompanies this textual description.

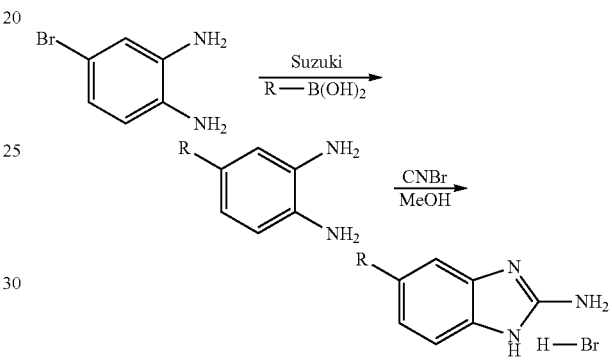

Step 1-C: Alternate synthesis of a substituted 2-aminobenzimidazole. A mixture of 5-fluoro-2-nitro-phenylamine (1 mmol), an alcohol (2 mmol), and potassium tert-butoxide (3 mmol) in THF (20 mL) are heated at about 60° C. overnight. After cooling the mixture to room temperature, water is added and then the mixture is extracted with ethyl acetate. The organic layer is washed with brine and dried over Na$_2$SO$_4$ and then concentrated. The crude material is purified on a silica gel column to yield a 5-alkyloxy-2-nitro-phenylamine. The 5-alkyloxy-2-nitro-phenylamine (1.0 mmol) is dissolved in an ethyl acetate-methanol mixture (about 1:1, 10 mL) in a round-bottom flask. To this solution Pd—C is added, and the mixture is stirred under a hydrogen atmosphere, while monitoring the reaction with thin-layer chromatography (TLC). After TLC shows substantial completion of the reaction, the solution is filtered on celite and then washed with methanol and concentrated to obtain a 4-alkyloxy-benzene-1,2-diamine. The 4-alkyloxy-benzene-1,2-diamine (1 mmol) is dissolved in ethanol and CNBr (1.5 mmol) is added. The resulting dark brown solution is heated at 60° C. for 30 minutes. Thereafter, the mixture is cooled to room temperature, and the solvent is evaporated. Then the mixture is co-evaporated with toluene about two times to obtain a 5-alkyloxy-1H-benzoimidazol-2-ylamine as a hydrobromide salt. The reaction scheme below provides an illustration that accompanies this textual description.

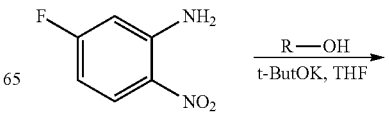

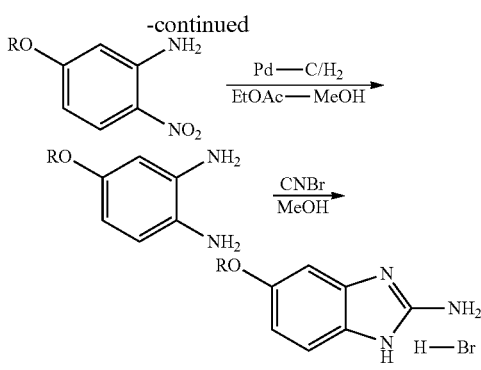

Step 1-D: Alternate synthesis of a substituted 2-aminobenzimidazole. A mixture of 5-fluoro-2-nitro-phenylamine (1 mmol), an amine (2 mmol) in THF (20 mL) is heated at about 60° C. overnight. After cooling the mixture to room temperature, the reaction mixture is concentrated. The crude material is purified on a silica gel column to yield a 5-amino-2-nitro-phenylamine. The 5-amino-2-nitro-phenylamine (1.0 mmol) is dissolved in an ethyl acetate-methanol mixture (about 1:1, 10 mL) in a round-bottom flask. To this solution Pd—C is added, and the mixture is stirred under a hydrogen atmosphere, while monitoring the reaction with thin-layer chromatography (TLC). After TLC shows completion of the reaction, the solution is filtered on celite and then washed with methanol and concentrated to obtain a 4-amino-benzene-1,2-diamine. The 4-amino-benzene-1,2-diamine (1 mmol) is dissolved in ethanol and CNBr (1.5 mmol) is added. The resulting dark brown solution is heated at 60° C. for 30 minutes. Thereafter, the mixture is cooled to room temperature, and the solvent is evaporated. Then, the mixture is co-evaporated with toluene about two times to obtain a 5-amino-1H-benzoimidazol-2-ylamine as a hydrobromide salt. The reaction scheme below provides an illustration that accompanies this textual description.

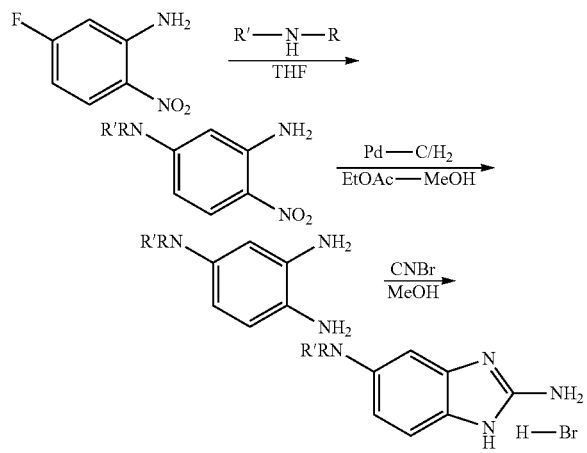

Step 2: Synthesis of a substituted 2-aminobenzimidazole amide. A mixture of a carboxylic acid (1 mmol), HBTU (1 mmol) and DIEA (3 mmol) in DMF (3 mL) is heated at 80° C. for 10 minutes. To this reaction mixture a substituted 2-aminobenzimidazole hydrobromide salt (1 mmol) is added, and the mixture continues to be heated at 80° C. for 30 minutes. After cooling the reaction mixture to room temperature, an aqueous sodium bicarbonate solution is added, and the mixture is stirred for 30 minutes. The mixture is then filtered, washed with water, and purified on silica gel column to yield a substituted 2-aminobenzimidazole amide. The reaction scheme below provides an illustration that accompanies this textual description.

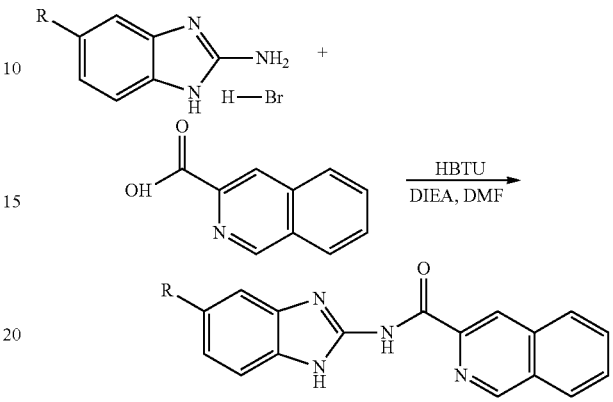

Example Compounds

Table 1 shows examples of compounds of Formula (I) or pharmaceutically acceptable salts thereof that were synthesized. Each of the identified compounds constitutes a separate embodiment of the invention, where the embodiments include the compound in its free (non-salted) form, tautomers of the compound in its free (non-salted) form, and pharmaceutically acceptable salts of either of the foregoing. In other embodiments, each of the recited compounds is in its free (non-salted) form constitutes a separate embodiment of the invention, including tautomers of each of the compounds. In other embodiments, the pharmaceutically acceptable salts of each of the recited compounds constitute a separate embodiment of the invention, including pharmaceutically acceptable salts of the tautomers of each of the compounds. Table 1 shows LC-MS data for each compound. The recorded m/z data are accurate to within about 1 amu. For some examples, proton NMR spectra were also recorded. For the NMR spectra, the peaks are reported relative to tetramethylsilane (TMS) unless otherwise indicated. Table 1 shows a generic structure, and identifies each compound by the identity of its substituents.

TABLE 1

| Example | $R^{101}$ | LCMS (m/z) | $^1$H NMR (400 MHz, DMSO-$d_6$) δ (ppm) |
|---|---|---|---|
| 1 | —O—CH$_2$-phenyl | 394.8 | 5.10 (2 H, s), 6.82-6.85 (1 H, m), 7.13 (1 H, d), 7.29-7.32 (1 H, m), 7.36-7.40 (3 H, m), 7.45-7.47 (2 H, m), 7.84-7.92 (2 H, m), 8.29 (2 H, t), 8.71 (1 H, s), 9.47 (1 H, s), 11.25 (1 H, s), 12.24 (1 H, s) |
| 2 | —O—(CH$_2$)$_2$-phenyl | 408.7 | 3.04 (2 H, t), 4.18 (2 H, t), 6.73-6.76 (1 H, m), 7.06 |

TABLE 1-continued

Structure: R^101-substituted benzimidazol-2-yl amide of isoquinoline-3-carboxylic acid

| Example | R^101 | LCMS (m/z) | ^1H NMR (400 MHz, DMSO-d_6) δ (ppm) |
|---|---|---|---|
| | | | (s, 1 H), 7.21-7.23 (1 H, m), 7.28-7.38 (5 H, m), 7-85-7.95 (2 H, m), 8.29 (2 H, t), 8.77 (1 H, s), 9.48 (1 H, s), 11.23 (1 H, d), 12.72 (1 H, s) |
| 3 | —O—CH_2-(4-CF_3-phenyl) | 462.7 | 5.23 (2 H, s), 6.85-6.87 (1 H, d), 7.58 (2 H, d), 7.64 (2 H, d), 7-76-7.85 (2 H, m), 8.03-8.10 (2 H, m), 8.71 (1 H, s), 8.24 (1 H, s), 11.14 (2 H, d) |
| 4 | —O—CH_2-(4-F-phenyl) | 412.7 | 5.06 (2 H, s), 6.92-6.95 (1 H, m), 7.05-7.09 (2 H, m), 7.42-7.45 (2 H, m), 7-75-7.84 (2 H, m), 8.02-8.09 (2 H, m), 8.71 (1 H, s), 8.22 (1 H, s), 11.12 (2 H, s) |
| 5 | —O—CH_2-(2,4-di-F-phenyl) | 431.8 | 5.11 (s, 2H), 6.83 (d, 1H), 7.09-7.17 (m, 2H), 7.27-7.42 (m, 1H), 7.40 (d, 1H), 7.5-7.7 (m, 1H), 7.86-7.96 (m, 2H), 8.30 (t, 2H), 8.78 (s, 1H), 9.49 (s, 1H), 11.25 (brs, 1H), 12.27 (brs, 1H) |
| 6 | —O—(CH_2)_2-cyclopentyl | 401.8 | 1.08-1.21 (m, 2H), 1.42-1.65 (m, 4H), 1.70-1.81 (m, 4H), 1.85-2.01 (m, 1H), 3.96 (t, 2H), 6.7-6.8 (m, 1H), 7.04 (s, 1H), 7.36 (d, 1H), 7.83-7.96 (m, 2H), 8.25-8.32 (m, 2H), 8.77 (s, 1H), 9.48 (s, 1H), 11.25 (brs, 1H), 12.20 (brs, 1H) |
| 7 | 4-phenyl-piperidin-1-yl | 448.8 | 1.78-1.92 (m, 4H), 2.6-2.7 (m, 1H), 2.7-2.8 (m, 2H), 3.64-3.70 (m, 2H), 6.90-6.94 (m, 1H), 7.08 (s, 1H), 7.15-7.25 (m, 1H), 7.28-7.38 (m, 5H), 7.84-7.98 (m, 2H), 8.26-8.34 (m, 2H), 8.78 (s, 1H), 9.49 (s, 1H), 11.2 (brs, 1H), 12.12 (brs, 1H) |
| 8 | —O—(CH_2)_3-phenyl | 423.9 | 9.23 (1H, s), 8.73 (1H, s), 8.02-8.10 (2H, m), 7.75-7.84 (2H, m), 7.39 (1H, bs), 7.20-7.35 (7H, m), 7.00 (1H, bs), 6.84 (1H, d), 3.97-4.02 (2H, m), 2.78-2.90 (2H, m), 2.04-2.18 (2H, m); in CDCl_3 |
| 9 | phenyl | 365.7 | 7.32-7.36 (1 H, m), 7.44-7.49 (3 H, m), 7.60 (1 H, s), 7.65-7.67 (2 H, m), 7-75-7.87 (3 H, m), 8.05-8.12 (2 H, m), 8.74 (1 H, s), .9.27 (1 H, s); in CDCl_3 |
| 10 | 3-(OCH_3)-phenyl | 395.8 | — |
| 11 | —NH—CH_2-phenyl | 393.7 | 4.38 (2 H, s), 6.88 (2 H, d), 7.24 (1 H, t), 7.29-7.34 (3 H, m), 7.38 (2 H, d), 7.47-7.50 (1 H, m), 7.92-7.99 (2 H, m), 8.35 (2 H, t), 8.86 (1 H, s), 9.56 (s, 1H) |
| 12 | —N(—CH_2-phenyl)_2 | 483.7 | — |

Compounds in Table 1 having a basic group or acidic group are depicted as the free base or acid. Depending on the reaction conditions and purification conditions, various compounds in Table 1 having a basic group may have been isolated in either the free base form, as a salt (such as an HCl salt), or in both forms.

Table 2 shows conventional names for the Examples shown in Table 1 above.

TABLE 2

| Example | Name |
|---|---|
| 1 | Isoquinoline-3-carboxylic acid (5-benzyloxy-1H-benzoimidazol-2-yl)-amide |
| 2 | Isoquinoline-3-carboxylic acid (5-phenethyloxy-1H-benzoimidazol-2-yl)-amide |
| 3 | Isoquinoline-3-carboxylic acid [5-(4-trifluoromethyl-benzyloxy)-1H-benzoimidazol-2-yl]-amide |
| 4 | Isoquinoline-3-carboxylic acid [5-(4-fluoro-benzyloxy)-1H-benzoimidazol-2-yl]-amide |
| 5 | Isoquinoline-3-carboxylic acid [5-(2,4-difluoro-benzyloxy)-1H-benzoimidazol-2-yl]-amide |
| 6 | Isoquinoline-3-carboxylic acid [5-(2-cyclopentyl-ethoxy)-1H-benzoimidazol-2-yl]-amide |
| 7 | Isoquinoline-3-carboxylic acid [5-(4-phenyl-piperidin-1-yl)-1H-benzoimidazol-2-yl]-amide |
| 8 | Isoquinoline-3-carboxylic acid [5-(3-phenyl-propoxy)-1H-benzoimidazol-2-yl]-amide |
| 9 | Isoquinoline-3-carboxylic acid (5-phenyl-1H-benzoimidazol-2-yl)-amide |
| 10 | Isoquinoline-3-carboxylic acid [5-(3-methoxy-phenyl)-1H-benzoimidazol-2-yl]-amide |
| 11 | Isoquinoline-3-carboxylic acid (5-benzylamino-1H-benzoimidazol-2-yl)-amide |
| 12 | Isoquinoline-3-carboxylic acid (5-dibenzylamino-1H-benzoimidazol-2-yl)-amide |

As shown in Table 3, below, compounds of the invention inhibit β-secretase enzyme activity. Compounds that inhibit β-secretase enzyme activity are potentially useful in treating diseases or conditions that may be associated with the build-up of β-amyloid plaques, including, but not limited to, Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases.

The compounds of Formula (I), tautomers of compounds of Formula (I), and/or pharmaceutically acceptable salts of either of the foregoing, may therefore be useful in the treatment of one or more of these diseases.

In one embodiment, the present invention provides a pharmaceutical composition comprising a compound of Formula (I), a tautomer of a compound of Formula (I), or pharmaceutically acceptable salts of either of the foregoing. In another embodiment, the present invention provides a pharmaceutical composition comprising a compound, tautomer, or pharmaceutically acceptable salt of any one of embodiments 1 to 61 (recited above). In another embodiment, the pharmaceutical composition comprises a compound, tautomer, or pharmaceutically acceptable salt of any one of embodiments 1 to 61 and a pharmaceutically acceptable carrier, excipient, diluent, or a mixture thereof.

In an embodiment, the pharmaceutical compositions containing a compound of Formula (I), a tautomer of a compound of Formula (I), or a pharmaceutically acceptable salt of either of the foregoing, may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

In another embodiment, formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

In another embodiment, the composition may comprise an aqueous suspension. Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Also, oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

In another embodiment, the pharmaceutical compositions of the present invention may comprise a syrup or elixir. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The pharmaceutical compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

In an embodiment, for topical use, creams, ointments, jellies, solutions of suspensions, etc., containing the compounds of the invention may be employed. For the purpose of this application, topical applications shall include mouth washes and gargles.

In an embodiment, the compounds of Formula (I), tautomers of compounds of Formula (I), or pharmaceutically acceptable salts of either of the foregoing may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutically-acceptable salts of compounds of Formula (I) or tautomers of compound of Formula (I), where a basic or acidic group is present in the structure, are also included within the scope of the invention. The term "pharmaceutically acceptable salts" refers to salts of the compounds of this invention which are not biologically undesirable and are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, there can be formed an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, Vol. 66, p. 1-19 (1977).

In another embodiment, the invention provides a pharmaceutical composition comprising a compound of Formula (I), a tautomer of a compound of Formula (I), or a pharmaceutically acceptable salt of either of the foregoing, and one or more pharmaceutically acceptable carriers, excipients, or diluents. In another embodiment, the invention provides a pharmaceutical composition comprising a compound, tautomer, or pharmaceutically acceptable salt of any one of embodiments 1 to 61 and one or more pharmaceutically acceptable carriers, excipients, or diluents.

In another embodiment, the present invention provides a compound of Formula (I), a tautomer of a compound of Formula (I), or a pharmaceutically acceptable salt of either of the foregoing for use in medicine. In another embodiment, the invention provides a compound, tautomer, or pharmaceutically acceptable salt of any one of embodiments 1 to 61 for use in medicine.

The present invention further provides for the use of a compound of Formula (I), a tautomer of a compound of Formula (I), or a pharmaceutically acceptable salt of either of the foregoing, in combination with one or more medically effective active compounds for simultaneous, subsequent, or sequential administration. The invention also provides for the use of a compound, tautomer, or pharmaceutically acceptable salt of any one of embodiments 1 to 61 in combination with one or more medically effective active compounds for simultaneous, subsequent, or sequential administration.

Examples of such medically effective active ingredients include, but are not limited to, β-secretase inhibitors, γ-secretase inhibitors, HMG-CoA reductase inhibitors, non-steroidal anti-inflammatory drugs (NSAIDs) (including but not limited to ibuprofen, naproxen, and diclofenac), N-methyl-D-aspartate (NMDA) receptor agonists (including but not limited to memantine), cholinesterase inhibitors (including but not limited to galantamine, rivastigmine, donepezil, and tacrine), vitamin E, CB-1 receptor antagonists, CB-1 receptor inverse agonists, antibiotics (including but not limited to doxycycline and rifampin), agents that bind Aβ or that induce antibodies that bind Aβ, anti-Aβ antibodies, Aβ vaccines, RAGE/RAGE ligand interaction antagonists, and other drugs that affect receptors or enzymes that either increase the efficacy, safety, convenience, or reduce unwanted side effects or toxicity of the compounds of the present invention. In one embodiment, the invention provides a pharmaceutical composition comprising a compound, tautomer, or pharmaceutically acceptable salt of any one of embodiments 1 to 61 and at least one other medically effective active ingredient selected from β-secretase inhibitors, γ-secretase inhibitors, HMG-CoA reductase inhibitors, non-steroidal anti-inflammatory drugs (NSAIDs) (including but not limited to ibuprofen, naproxen, and diclofenac), N-methyl-D-aspartate (NMDA) receptor agonists (including but not limited to memantine), cholinesterase inhibitors (including but not limited to galantamine, rivastigmine, donepezil, and tacrine), vitamin E, CB-1 receptor antagonists, CB-1 receptor inverse agonists, antibiotics (including but not limited to doxycycline and rifampin), agents that bind Aβ or that induce antibodies that bind Aβ, anti-Aβ antibodies, Aβ vaccines, and RAGE/RAGE ligand interaction antagonists. In another embodiment, the invention provides for the use of a compound, tautomer, or pharmaceutically acceptable salt of any one of embodiments 1 to 61 in combination with at least one other medically effective active ingredient selected from β-secretase inhibitors, γ-secretase inhibitors, HMG-CoA reductase inhibitors, non-steroidal anti-inflammatory drugs (NSAIDs) (including but not limited to ibuprofen, naproxen, and diclofenac), N-methyl-D-aspartate (NMDA) receptor agonists (including but not limited to memantine), cholinesterase inhibitors (including but not limited to galantamine, rivastigmine, donepezil, and tacrine), vitamin E, CB-1 receptor antagonists, CB-1 receptor inverse agonists, antibiotics (including but not limited to doxycycline and rifampin), agents that bind Aβ or that induce antibodies that bind Aβ, anti-Aβ antibodies, Aβ vaccines, and RAGE/RAGE ligand interaction antagonists, for simultaneous, subsequent, or sequential administration.

Methods of Use

A compound of Formula (I) or pharmaceutically acceptable salt thereof, or a pharmaceutical composition comprising a compound of Formula (I), a tautomer of a compound of Formula (I), or a pharmaceutically acceptable salt of either of the foregoing, may be used for the treatment of a disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases.

In one embodiment, the invention provides a method of treatment comprising administering a compound, tautomer, or pharmaceutically acceptable salt of any one of embodiments 1 to 61 to a human. In another embodiment, the invention provides a method of treatment comprising administering at least 0.1 milligrams of a compound, tautomer, or pharmaceutically acceptable salt of any one of embodiments 1 to 61 to a human.

In another embodiment, the invention provides a method of treatment comprising administering a compound, tautomer, or pharmaceutically acceptable salt of any one of embodiments 1 to 61 to a human, so as to treat at least one disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases. In another embodiment, the invention provides a method of treatment comprising administering a compound, tautomer, or pharmaceutically acceptable salt of any one of embodiments 1 to 61 to a human, so as to treat Alzheimer's disease. In another embodiment, the invention provides a method of treatment comprising administering a compound, tautomer, or pharmaceutically acceptable salt of any one of embodiments 1 to 61 to a human, so as to treat mild cognitive impairment. In another embodiment, the invention provides a method of treatment comprising administering a compound, tautomer, or pharmaceutically acceptable salt of any one of embodiments 1 to 61 to a human, so as to treat dementia of Alzheimer's type. In another embodiment, the invention provides a method of treatment comprising administering a compound, tautomer, or pharmaceutically acceptable salt of any one of embodiments 1 to 61 to a human, so as to treat cerebral amyloid angiopathy.

As used herein, "Alzheimer's Disease" is a disorder that may be diagnosed by NINCDS and DSM criteria, Mini-Mental State Examination, and Clinical Dementia Rating within particular limits.

In another embodiment, the invention provides a method of treatment comprising administering a compound, tautomer, or pharmaceutically acceptable salt of any one of embodiments 1 to 61 to a human, so as to improve cognitive performance. Cognitive performance may be assessed with the cognitive subscale of the Alzheimer's Disease Assessment Scale (ADAS-cog), as is known in the art, which scores cognitive function on a 0 to 70 scale, with higher scores indicating greater cognitive impairment. Thus, a reduction in score demonstrates cognitive improvement. In another embodiment, the invention provides a method of treatment comprising administering a compound, tautomer, or pharmaceutically acceptable salt of any one of embodiments 1 to 61 to a human, so as to reduce an ADAS-cog score in a subject with an abnormally high score. In another embodiment, the invention provides a method of treatment comprising administering a compound, tautomer, or pharmaceutically acceptable salt of any one of embodiments 1 to 61 to a human so as to maintain an ADAS-cog score in a subject. In another embodiment, the invention provides a method of treatment comprising administering a compound, tautomer, or pharmaceutically acceptable salt of any one of embodiments 1 to 61 to a human, so as to decrease the rate of increase in an ADAS-cog score in a subject. In each of these embodiments, the subject may be suffering from dementia of the Alzheimer's type. In a further embodiment, the subject may be suffering from dementia of the Alzheimer's type with early onset uncomplicated, dementia of the Alzheimer's type with early onset with delusions, dementia of the Alzheimer's type with early onset with depressed mood, dementia of the Alzheimer's type with late onset uncomplicated, dementia of the Alzheimer's type with late onset with delusions, or dementia of the Alzheimer's type with late onset with depressed mood.

In addition, the progression of Alzheimer's Disease may also be assessed through examination of four areas of patient function: General, Cognitive, Behavioral, and Activities of Daily Living. Such an assessment may be performed using a Clinician's Interview Based Impression of Change (CIBIC or CIBIC plus). In another embodiment, the present invention provides a method for improvement in a subject's function comprising administering a compound, tautomer, or pharmaceutically acceptable salt of any one of embodiments 1 to 61 to a human. In an embodiment, the subject's function is one or more of general, cognitive, behavioral, and activities of daily living.

In another embodiment, the invention provides a compound, tautomer, or pharmaceutically acceptable salt of any one of embodiments 1 to 61 for use in medicine. In another embodiment, the invention provides a compound, tautomer, or pharmaceutically acceptable salt of any one of embodiments 1 to 61 for use in the treatment of at least one disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases. In another embodiment, the invention provides a compound, tautomer, or pharmaceutically acceptable salt of any one of embodiments 1 to 61 for use in the treatment of Alzheimer's disease. In another embodiment, the invention provides a compound, tautomer, or pharmaceutically acceptable salt of any one of embodiments 1 to 61 for use in the treatment of mild cognitive impairment. In another embodiment, the invention provides a compound, tautomer, or pharmaceutically acceptable salt of any one of embodiments 1 to 61 for use in the treatment of dementia of Alzheimer's type. In another embodiment, the invention provides a compound, tautomer, or pharmaceutically acceptable salt of any one of embodiments 1 to 61 for use in the treatment of cerebral amyloid angiopathy.

In another embodiment, the invention provides a compound, tautomer, or pharmaceutically acceptable salt of any one of embodiments 1 to 61 for use in the prevention of at least one disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases. In another embodiment, the invention provides a compound, tautomer, or pharmaceutically acceptable salt of any one of embodiments 1 to 61 for use in the prevention of Alzheimer's disease. In another embodiment, the invention provides a compound, tautomer, or pharmaceutically acceptable salt of any one of embodiments 1 to 61 for use in the prevention of mild cognitive impairment. In another embodiment, the invention provides a compound, tautomer, or pharmaceutically acceptable salt of any one of embodiments 1 to 61 for use in the prevention of dementia of Alzheimer's type. In another embodiment, the invention provides a compound, tautomer, or pharmaceutically acceptable salt of any one of embodiments 1 to 61 for use in the prevention of cerebral amyloid angiopathy.

In another embodiment, the invention provides a compound, tautomer, or pharmaceutically acceptable salt of any one of embodiments 1 to 61 for use in the improvement of cognitive performance. In another embodiment, the invention provides a compound, tautomer, or pharmaceutically acceptable salt of any one of embodiments 1 to 61 for use in the reduction of an ADAS-cog score in a subject with an abnormally high score. In another embodiment, the invention provides a compound, tautomer, or pharmaceutically acceptable salt of any one of embodiments 1 to 61 for use in the maintenance of an ADAS-cog score in a subject. In another embodiment, the invention provides a compound, tautomer, or pharmaceutically acceptable salt of any one of embodiments 1 to 61 for use in decreasing the rate of increase in an ADAS-cog score in a subject. In another embodiment, the invention provides a compound, tautomer, or pharmaceutically acceptable salt of any one of embodiments 1 to 61 for use in the improvement of subject function in one or more of general, cognitive, behavioral, and activities of daily living.

In another embodiment, the invention provides for the use of a compound, tautomer, or pharmaceutically acceptable salt of any one of embodiments 1 to 61 for the preparation of a medicament. In another embodiment, the invention provides for the use of a compound, tautomer, or pharmaceutically acceptable salt of any one of embodiments 1 to 61 for the preparation of a medicament for the treatment of at least one disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases. In another embodiment, the invention provides for the use of a compound, tautomer, or pharmaceutically acceptable salt of any one of embodiments 1 to 61 for the preparation of a medicament for the treatment of Alzheimer's disease. In another embodiment, the invention provides for the use of a compound, tautomer, or pharmaceutically acceptable salt of any one of embodiments 1 to 61 for the preparation of a medicament for the treatment of mild cognitive impairment. In another embodiment, the invention provides for the use of a compound, tautomer, or pharmaceutically acceptable salt of any one of embodiments 1 to 61 for the preparation of a medicament for the treatment of dementia of Alzheimer's type. In another embodiment, the invention provides for the use of a compound, tautomer, or pharmaceutically acceptable salt of any one of embodiments 1 to 61 for the preparation of a medicament for the treatment of cerebral amyloid angiopathy.

In another embodiment, the invention provides for the use of a compound, tautomer, or pharmaceutically acceptable salt of any one of embodiments 1 to 61 for the preparation of a medicament for improving cognitive performance. In another embodiment, the invention provides for the use of a compound, tautomer, or pharmaceutically acceptable salt of any one of embodiments 1 to 61 for the preparation of a medicament for reducing an ADAS-cog score in a subject with an abnormally high score. In another embodiment, the invention provides for the use of a compound, tautomer, or pharmaceutically acceptable salt of any one of embodiments 1 to 61 for the preparation of a medicament for the maintaining an ADAS-cog score in a subject.

In another embodiment, the invention provides for the use of a compound, tautomer, or pharmaceutically acceptable salt of any one of embodiments 1 to 61 for the preparation of a medicament for decreasing the rate of increase in an ADAS-cog score in a subject. In another embodiment, the invention provides for the use of a compound, tautomer, or pharmaceutically acceptable salt of any one of embodiments 1 to 61 for the preparation of a medicament for improving subject function in one or more of general, cognitive, behavioral, and activities of daily living.

In another embodiment, the present invention provides a method for inhibiting the interaction of BACE with a physiological ligand. An example of a physiological ligand of BACE includes, but is not limited to, amyloid precursor protein (APP). In one embodiment, the invention provides a method for treating Alzheimer's Disease or dementia of the Alzheimer's type comprising: administering a compound, tautomer, or pharmaceutically acceptable salt of any one of embodiments 1 to 61 to a human, so as to inhibit the interaction of BACE with a physiological ligand. In one embodiment, the physiological ligand is amyloid precursor protein (APP). In a further embodiment, the invention provides a compound, tautomer, or pharmaceutically acceptable salt of any one of embodiments 1 to 61 for use in the inhibition of the interaction of BACE with a physiological ligand. In a further embodiment, the invention provides for the use of a compound, tautomer, or pharmaceutically acceptable salt of any one of embodiments 1 to 61 for the preparation of a medicament for inhibiting the interaction of BACE with a physiological ligand.

In another embodiment, the present invention provides a method for increasing the α-secretory pathway in a human subject. In one embodiment, the invention provides a method for treating Alzheimer's Disease or dementia of the Alzheimer's type comprising: administering a compound, tautomer, or pharmaceutically acceptable salt of any one of embodiments 1 to 61 to a human, so as to increase the α-secretory pathway. In a further embodiment, the invention provides a compound, tautomer, or pharmaceutically acceptable salt of any one of embodiments 1 to 61 for use in increasing the α-secretory pathway in a human subject. In a further embodiment, the invention provides for the use of a compound, tautomer, or pharmaceutically acceptable salt of any one of embodiments 1 to 61 for the preparation of a medicament for increasing the α-secretory pathway in a human subject.

In each of the methods or uses described above, a compound, tautomer, or pharmaceutically acceptable salt of any of embodiments 1 to 61 may be administered to a subject as part of a pharmaceutically formulation, as described above.

Examples of compounds of Formula (I), tautomers of compounds of Formula (I), or pharmaceutically acceptable salts of either of the foregoing, of the present invention having potentially useful biological activity are listed by name below in Table 3. The ability of compounds Formula (I), tautomers of compounds of Formula (I), or a pharmaceutically acceptable salt of either of the foregoing, to inhibit the proteolytic activity of BACE was established with the representative compounds of Formula (I) listed in Table 3 using the enzyme and cell based assays described below.

Biological Assays

The following assay methods were used to identify and evaluate compounds of Formula (I) that are effective in reducing the proteolytic activity of BACE.

BACE Fluorescence Resonance Energy Transfer (FRET) Assay

In the following assay, the proteolytic activity of BACE is measured by observing cleavage of a fluorescent group from a peptide substrate containing a rhodamine fluorescent donor and a quenching acceptor.

The inhibitory activity of compounds of Formula (I) may be compared to a statine derived control inhibitor STA200 (MP Biomedical Cat. #STA-200). The cleavage reaction occurs when a BACE-1 substrate (Invitrogen, Cat. #P2986) was added to a reaction mixture containing BACE-1 enzyme (R & D Systems, Cat. #931AS) and allowed to proceed for 1.5 hours. Fluorescence, used as a marker of BACE activity, is monitored using 540 nm excitation and 585 nm emission wavelengths (Envision, Perkin Elmer).

A typical assay reaction contains BACE-1 enzyme—in assay buffer (50 mM sodium acetate, pH 4-4.5, 0.01% CHAPS (3-[(3-Cholamidopropyl)dimethylammonio]-1-propanesulfonate), 0.0125% TritonX-100, 0.006% EDTA) which is pre-incubated for 30 minutes with test compound in 7.5% DMSO. The reaction is initiated with the addition of BACE-1 substrate in assay buffer and allowed to proceed for 1.5 hours at room temperature. Assays are conducted in black 384-well microtiter plates and scanned at room temperature using 540 nm excitation and 585 nm emission wavelengths.

A test compound's activity is reported as the $IC_{50}$.

Aβ Cell Based Assay Procedure

In the following assay, the proteolytic activity of BACE in cells exposed to varying concentrations of a compound of interest is measured by observing the amount of $A\beta_{1-40}$ secreted from HEK293 cells (Human Embryonic Kidney epithelial cell line) stably expressing wildtype human APP695 protein (HEK-APPwt cells).

HEK-APPwt cells were grown in high glucose DMEM (Dulbecco's Modified Eagles Medium SIGMA Cat. #D5796) supplemented with 25 mM HEPES (4-(2-hydroxyethyl)-1-piperazineethanesulfonic acid) (pH 7.4) (Invitrogen Cat. #15630-114), 0.1 mM NEAA (Non-essential Amino Acids) (BioWhittaker Cat. #13-114E), 10% fetal bovine serum (SIGMA Cat. #F4135) and 250 μg/mL hygromycin (Invitrogen Cat. #10687-010) in T-225 flasks at 37° C. with 5% $CO_2$ and humidity control.

Test compounds were initially prepared in DMSO and diluted with DMEM media containing 2% FBS (Fetal bovine serum). Ten standard compound solutions were prepared having a range of concentrations. The standard compound solutions were used to determine the $EC_{50}$ of the test compound. The range of concentrations chosen may depend on the compound's predicted potency.

To prepare the cells for the assay, a flask containing HEK-APPwt cells were trypsinized briefly (1 mL trypsin), and once the cells detached, 4 mL of 10% FBS-DMEM was added to the flask. The detached cells were centrifuged at 900 rpm for 5 min to form a pellet.

The HEK-APPwt cell pellet was re-suspended with 10 mL DMEM media containing 2% FBS. 80 μL of the cell suspension was added to each well of a 96-well cell culture plate to give $100 \times 10^4$ cells/mL. 10 μL of a standard compound solution was added to each well of the 96-well cell culture plate followed by 10 μL of Alamar blue solution. The cells were incubated at 37° C. in a 5% $CO_2$ incubator for 6 hours.

At the end of the incubation, the plates were removed from incubator, and the supernatant was collected. $A\beta_{1-40}$ concentration in the medium was measured by using a commercial $A\beta_{1-x}$ ELISA kit (IBL, Japan Cat. #27729). Briefly, the ELISA plates were coated with an anti-human Aβ (N)(82E1) mouse IgG monoclonal antibody. A horseradish peroxidase conjugated anti-human Aβ11-28 mouse IgG monoclonal antibody was used for detection. The cell culture supernatant was diluted with EIA buffer+protease inhibitors (kit buffer containing protease inhibitors (1 mL PI/30 mL buffer)). A 100 μL aliquot of the diluted supernatant was added to each well of the ELISA plate and incubated for 6 hrs at 4° C. The ELISA plate was washed 8 times with phosphate buffered saline (PBS) containing 0.05% Tween 20.

A 100 μL of detection antibody was then added and incubated for 1 hour at 4° C. The plate was washed 8 times with PBS buffer containing 0.05% Tween 20 followed by addition of 100 μL of the chromogen tetramethylbenzidine (TMB). The plate was incubated in the dark at room temperature for about 30 min and a stop solution (1N $H_2SO_4$) was added.

The intensity of the color developed was measured at 450 nm. The optical density at 450 nm (OD450) is proportional to the concentration of human $A\beta_{1-40}$ secreted by the cell. As a reference, N—[N-(3,5-difluorophenacetyl-L-alanyl)]-S-phenylglycine t-butyl ester (DAPT, a γ-secretase inhibitor) was used to indicate 100% inhibition of BACE activity. Thus, the assay measures the ability of a compound of interest to reduce $A\beta_{1-40}$ secretion. Compound potency was reported as the $EC_{50}$ by calculating the percent inhibition at all concentration levels and the data were fit with non-linear curve fitting algorithm using in GraphPad Prism.

Table 3

| Example | $IC_{50}$ (μM) FRET | $EC_{50}$ (μM) Cell-Based |
|---|---|---|
| 1 | 0.085 | 0.12 |
| 2 | 0.19 | 2.00 |
| 3 | 0.95 | 0.55 |
| 4 | 0.10 | 0.16 |
| 5 | 0.86 | 1.20 |
| 6 | 0.26 | 0.16 |
| 7 | 0.10 | 1.40 |
| 8 | 0.47 | 1.20 |
| 9 | 0.19 | 1.09 |
| 10 | 0.16 | 1.00 |
| 11 | 0.13 | 0.60 |
| 12 | 0.38 | 2.30 |

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the subject being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Moreover, all compounds that are recited in the written description are contemplated as possibilities for any of the recited methods, processes, compositions, and/or compounds as appear in the written description and the appended claims.

We claim:

1. A compound of Formula (I), a tautomer of a compound of Formula (I), or a pharmaceutically acceptable salt of either of the foregoing:

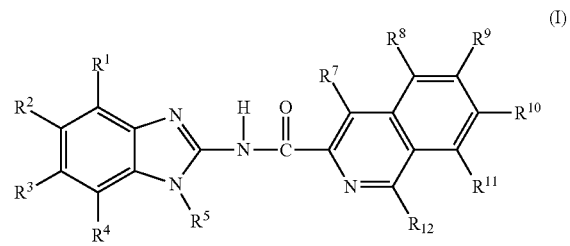

(I)

wherein $R^7$, $R^8$, $R^9$, $R^{10}$, $R^{11}$, and $R^{12}$ are hydrogen;

$R^1$ and $R^4$ are hydrogen;

one of $R^2$ and $R^3$ is $-L^2-D^2-G^2$, and the other is hydrogen;

wherein $L^2$ is a direct bond or —O—;

$D^2$ is a direct bond or -alkylene-;

$G^2$ is phenyl or cycloalkyl, wherein the phenyl and cycloalkyl groups are optionally substituted with one or more substituents independently selected from the group consisting of: -halo, -alkyl, -haloalkyl, —OH, —$NH_2$, -phenyl, -cycloalkyl, -alkylene-phenyl, -alkylene-cycloalkyl, —O-alkyl, —O-haloalkyl, —O-phenyl, —O-cycloalkyl, —O-alkylene-phenyl, —O-alkylene-cycloalkyl, —C(O)alkyl, and —C(O)haloalkyl; and $R^5$ is hydrogen.

2. The compound of claim 1, wherein $D^2$ is —CH$_2$— or —CH$_2$—CH$_2$—.

3. The compound of claim 2, wherein $G^2$ is phenyl, which is optionally substituted with one or more substituents independently selected from the group consisting of: -halo, -alkyl, -haloalkyl, —OH, —NH$_2$, -phenyl, -cycloalkyl, -alkylene-phenyl, -alkylene-cycloalkyl, —O-alkyl, —O-haloalkyl, —O-phenyl, —O-cycloalkyl, —O-alkylene-phenyl, —O-alkylene-cycloalkyl, —C(O)alkyl, and —C(O)haloalkyl.

4. The compound of claim 3, wherein $G^2$ is phenyl, wherein the phenyl group is unsubstituted.

5. The compound of claim 3, wherein $G^2$ is phenyl, which is optionally substituted with one or more substituents independently selected from the group consisting of: —F, —Cl, —C$_{1-3}$ alkyl, —CF$_3$, —O—C$_{1-3}$ alkyl, —O—CF$_3$, —CH$_2$—CF$_3$, and —C(O)—CF$_3$.

6. The compound of claim 2, wherein $G^2$ is cycloalkyl, which is optionally substituted with one or more substituents independently selected from the group consisting of: -halo, -alkyl, -haloalkyl, —OH, —NH$_2$, -phenyl, -cycloalkyl, -alkylene-phenyl, -alkylene-cycloalkyl, —O-alkyl, —O-haloalkyl, —O-phenyl, —O-cycloalkyl, —O-alkylene-phenyl, —O-alkylene-cycloalkyl, —C(O)alkyl, and —C(O)haloalkyl.

7. The compound of claim 6, wherein $G^2$ is cycloalkyl, wherein the cycloalkyl group is unsubstituted.

8. The compound of claim 7, wherein $G^2$ is a cyclopentyl or cyclohexyl.

9. A compound, which is a compound selected from the group consisting of:

Isoquinoline-3-carboxylic acid (5-benzyloxy-1H-benzoimidazol-2-yl)-amide;

Isoquinoline-3-carboxylic acid (5-phenethyloxy-1H-benzoimidazol-2-yl)-amide;

Isoquinoline-3-carboxylic acid [5-(4-trifluoromethyl-benzyloxy)-1H-benzoimidazol-2-yl]-amide;

Isoquinoline-3-carboxylic acid [5-(4-fluoro-benzyloxy)-1H-benzoimidazol-2-yl]-amide;

Isoquinoline-3-carboxylic acid [5-(2,4-difluoro-benzyloxy)-1H-benzoimidazol-2-yl]-amide;

Isoquinoline-3-carboxylic acid [5-(2-cyclopentyl-ethoxy)-1H-benzoimidazol-2-yl]-amide;

Isoquinoline-3-carboxylic acid [5-(3-phenyl-propoxy)-1H-benzoimidazol-2-yl]-amide;

Isoquinoline-3-carboxylic acid (5-phenyl-1H-benzoimidazol-2-yl)-amide; and

Isoquinoline-3-carboxylic acid [5-(3-methoxy-phenyl)-1H-benzoimidazol-2-yl]-amide;

or a tautomer thereof, or a pharmaceutically acceptable salt of any of the foregoing.

10. Isoquinoline-3-carboxylic acid (5-benzyloxy-1H-benzoimidazol-2-yl)-amide or a tautomer thereof, or a pharmaceutically acceptable salt of either of the foregoing.

11. Isoquinoline-3-carboxylic acid [5-(4-fluoro-benzyloxy)-1H-benzoimidazol-2-yl]-amide or a tautomer thereof, or a pharmaceutically acceptable salt of either of the foregoing.

12. Isoquinoline-3-carboxylic acid [5-(2-cyclopentyl-ethoxy)-1H-benzoimidazol-2-yl]-amide or a tautomer thereof, or a pharmaceutically acceptable salt of either of the foregoing.

13. A pharmaceutical composition comprising a compound of claim 1 and a pharmaceutically acceptable carrier, excipient, diluent, or a mixture thereof.

14. A pharmaceutical composition comprising a compound of claim 9 and a pharmaceutically acceptable carrier, excipient, diluent, or a mixture thereof.

15. A pharmaceutical composition comprising a compound of claim 10 and a pharmaceutically acceptable carrier, excipient, diluent, or a mixture thereof.

16. A pharmaceutical composition comprising a compound of claim 11 and a pharmaceutically acceptable carrier, excipient, diluent, or a mixture thereof.

17. A pharmaceutical composition comprising a compound of claim 12 and a pharmaceutically acceptable carrier, excipient, diluent, or a mixture thereof.

* * * * *